US006258531B1

(12) United States Patent
Bienhaus et al.

(10) Patent No.: US 6,258,531 B1
(45) **Date of Patent: *Jul. 10, 2001**

(54) METHOD OF ISOLATING A BIOLOGICAL MATERIAL

(75) Inventors: Gerhard Bienhaus, Wielenbach; Michael Fritz, Biblis; Jürgen Schwab, Ketsch; Edda Geisler, Mannheim; Herbert Harttig, Altrip; Heinz Macho, Fürth, all of (DE)

(73) Assignee: Roche Diagnostics GmbH, Mannheim (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/622,016

(22) Filed: Mar. 26, 1996

(30) Foreign Application Priority Data

Apr. 1, 1995 (DE) .............................................. 195 12 361

(51) Int. Cl.[7] .......................... C12Q 1/68; G01N 33/543; C07K 1/00; C07C 1/00

(52) U.S. Cl. ................................... 435/6; 435/4; 435/7.1; 435/262; 435/270; 436/518; 436/528; 436/807; 530/412; 530/413; 530/415

(58) Field of Search .................................... 435/262, 270, 435/4, 7.1, 6; 530/412, 413, 415; 436/518, 528, 807

(56) References Cited

U.S. PATENT DOCUMENTS

| | | | | |
|---|---|---|---|---|
| 4,021,352 | * | 5/1977 | Sarstedt | 210/359 |
| 4,644,807 | * | 2/1987 | Mar | 73/864.62 |
| 4,909,992 | * | 3/1990 | Bjorkman | 422/100 |
| 5,208,160 | * | 5/1993 | Kikyotani et al. | 435/270 |
| 5,339,829 | * | 8/1994 | Thieme et al. | 128/760 |
| 5,478,752 | * | 12/1995 | Lerch et al. | 436/169 |

FOREIGN PATENT DOCUMENTS

| | | | | |
|---|---|---|---|---|
| 9429721 | * | 12/1994 | (WO) | G01N/35/543 |

* cited by examiner

*Primary Examiner*—Rodney P. Swartz
(74) *Attorney, Agent, or Firm*—Arent Fox Kintner Plotkin & Kahn

(57) ABSTRACT

A method of isolating a biological material by a) providing a biological material which is bound to a porous matrix (C11), and b) compressing the matrix under conditions where the biological material is released from the surface of the matrix into an elution liquid.

brings about the advantage that the emission of aerosols into the environment is greatly reduced. It is also possible to obtain highly concentrated and minute amounts of solution. The method is also easy to automate.

5 Claims, 3 Drawing Sheets

METHOD OF ISOLATING A BIOLOGICAL MATERIAL

Subject matter of the invention is a method of isolating a biological material by binding said biological material to a solid phase, and releasing said material in a special procedure and a system suitable for isolating said biological material.

Recently, biological materials have gained increasing interest in many fields. This is facilitated by the fact that it has become possible over the last few decades to separate biological materials from other materials. Biological materials are generally available in a complex mixture together with other materials. Moreover, most biological materials are also present in very minute amounts compared to other components of a biological individual. Changes of biological materials with respect to its normal condition serve to diagnose the condition of the biological individual. Methods of analyzing biological materials are, hence, of particular interest in the field of molecular biology and health care. Depending on the required analysis, a more or less specific method of isolation is selected. There exists a multitude of isolation methods for biological materials which depend on the type of biological material to be isolated and its subsequent use. In the method used in the analysis of antigens and antibodies, the biological material (e.g. an antigen, antibody or nucleic acid) is bound to the non-porous inner wall of a cuvette made of glass or polystyrene. In this case, the binding of the biological material is so specific that the biological material to be detected is immobilized on the surface. This method does not propose to again release the biological material; this would even be adverse to the subsequent quantitative determination.

A second type of method uses swellable, porous materials to separate biological materials, e.g. according to their molecular weight. In this method, there is no binding between a biological material and a solid phase. The separation is essentially accomplished by using the different penetration properties of biological materials based on their different sizes.

A third kind of isolation method is based on the varying degree of binding of different biological materials to porous materials which exhibit a particular affinity to the biological material when specificity-enhancing groups are attached. This method makes use of column-like accumulations of particle-type affinity materials. A liquid which contains the biological material is made to pass through this accumulation of material. The biological material to be isolated is then bound to the surface of the porous particles on the groups with the affinity for the biological material; all other components emerge from the column together with the remaining liquid. In a subsequent step, the biological material is released from the porous material by allowing an elution to flow through the column in exactly the same direction which then releases the binding to the porous material. The biological material is then contained in the elution liquid.

In presently known methods, the elution liquid was passed through the porous matrix either by applying pressure in flow direction of the liquid, or even by centrifuging the column to spin the elution liquid out of the porous matrix. This method, however, requires the use of vacuum pumps or centrifuges, hence, instruments that are often used in medical routine diagnostics for this particular purpose. Moreover, the use of these instruments, especially centrifuges, is time-intensive and does not allow the continuous processing of samples.

It is an object of the present invention to provide a new method of isolation for biological material which brings about improvements with respect to those known in prior art.

Subject matter of the invention is a method of isolating a biological material by providing a biological material bound to a compressible porous matrix, and compressing the matrix under conditions where the biological material is released from the surface of the matrix into an elution liquid. Another subject matter of the invention is a system for isolating the biological material.

An isolation method as understood in the invention is a method where one or several components of the mixture are separated from the remaining components of this mixture. This covers in particular those methods where the one or several components to be separated are bound to a solid phase, where the remaining liquid is removed and the one or several bound components are subsequently released into another liquid.

Biological material is understood to be organic compounds that are in a relation to beings such as animals, humans, viruses, bacteria, or plants. They include, for example, the components found in such beings. Particularly preferred components are those that are present either in a dissolved form or can be dissolved in liquid, but can also be bound to a solid matrix. They include low-molecular substances, on the one hand, (with a molecular weight of less than 2000 D), such as vitamins, but also therapeutically active substances and hormones; further, they also include high-molecular substances (with a molecular weight of more than 2,000 D), such as biopolymers that consist of monomer units. They include, for example, proteins and nucleic acids. The method in accordance with the invention is particularly suitable for isolating nucleic acids. When dealing with proteins, the immunologically active substances, such as antigens and antibodies are particularly preferred.

Biological materials which can be isolated in a preferred manner are recovered from a liquid of the being in question and bound to a matrix. Depending on the part of the being from which the biological material is to be isolated, the being may be subject to a pretreatment. Such a pretreatment serves to release the biological material from the being. Such a pretreatment is necessary, for example, when the being is a bacterium or a group of bacteria. In this case, it is preferred to destroy the cells to allow the components of the being to be released into the liquid. Subsequently, the solid substances that may have formed can be separated. If the biological material is present in a liquid in an already accessible form, e.g. in a body fluid, cells or other substances that may interfere with the isolation of the biological material are often separated. This can be accomplished by means of filtration or by using affinity materials. In any case, the result of a pretreatment is always a sample liquid which contains the biological material in a form where it can be bound to a matrix.

In one step of the method of the invention, the biological material is provided in a form where it is bound to a compressible porous matrix. The matrix as understood in the invention is a non-soluble material present in the liquid containing the biological material. The chemical composition of the matrix is determined by the fact that the matrix must be compressible and porous, for which reason organic or inorganic polymers are used. Organic polymers include, for example, plastics such as polystyrene, but also cellulose, e.g. paper. Inorganic polymers are in particular substances which contain a certain percentage of glass. The matrix, can, however, also consist of a metal.

The compressible porous matrix in accordance with the invention is a spatially extending structure having a non-soluble part made of the above-mentioned material and a part which can be filled with liquid. This fillable part is in the following referred to as the inner volume. The inner volume extends between the non-soluble part thus forming a system of coherent porous and/or empty spaces. This system could preferably also be referred to as an open pore system.

The non-soluble part in the system also forms a spatially extending structure, which, in a preferred manner, has a coherent structure. It is possible, but not preferred, that the matrix be a multi-component system, e.g. a system where the particle-type component is sealed between two particle-type components in direction toward the interior (C14) and in direction of a liquid-permeable component, e.g. a fleece, at the lower opening in the structural form. The particle-type component can then assume the function of a slurry between the two components; in order to obtain the liquid, the two components are added to one another which then leads to a compression of the slurry and consequently reduces the liquid volume contained therein.

Examples for such a compressible porous matrix are sponge-type structures and structures consisting of fibers such as fleeces. In a preferred manner, the matrix is capable of absorbing liquid, it is also possible to apply sample liquid to its surface.

A compressible matrix as understood in the invention is one where the inner volume can be reduced by 50% or more, preferably 70% or more, or particularly preferred 90% or more, by pressing together the spatially extended structure of non-soluble part and inner volume. For practical reasons, it is unlikely that a complete elimination of the inner volume can be achieved; a certain percentage of inner volume and, hence, liquid will therefore remain in the matrix.

The percentage of volume of non-soluble material to inner volume preferably ranges between 10:1 and 1:100, particularly preferred between 1:1 and 1:50.

The compressibility of the porous matrix must not necessarily be reversible; i.e. when releasing the pressure exerted on the matrix, the latter must not necessarily resume its original shape. The extension of the matrix depends inter alia upon the amount of biological material to be bound. The outer form can be freely selected. It depends inter alia upon the type of immobilization of biological material and the subsequent release. A plate-like form of the matrix is preferred.

The non-soluble material of the matrix can already be selected such that the biological material exhibits a high affinity to this material, thus facilitating binding. Such a case is given for the immobilization of nucleic acids when a glass fiber fleece is used as the non-soluble material. It is known that all nucleic acids exhibit a certain affinity to glass surfaces. When the material itself does not exhibit any affinity to the biological material to be isolated, the surface of this material can be modified so as to allow binding. In the case that nucleic acids are to be bound, it is possible to bind so-called capture probes to the surface, i.e. nucleic acids which have a sequence that is complementary to the nucleic acid to be isolated. When immunologically reactive compounds are to be isolated, i.e. antigens or antibodies, it is possible to immbolize the corresponding immune partners, i.e. antigens or antigens. The binding of capture probes and/or immunoreactive compounds can be accomplished with the aid of methods that are also known for non-porous materials.

The biological material bound to the compressible porous matrix can be accomplished in that the matrix is brought into contact with the solution of the biological material and incubated for a sufficient period of time. Since the amount of solution in which the biological material is present usually exceeds the inner volume of the matrix, it is preferred to allow the solution to pass through the matrix, e.g. by drawing off or centrifugation. In a particularly preferred manner, the solution is pressed through the matrix in the vessel without applying low pressure or centrifugation. In a preferred manner, the liquid present in the interior of the matrix containing the components of the solution to be bound is subsequently removed from the matrix, e.g. also by drawing off, centrifuging or pressing. If desired, the matrix which now contains the biological material in a bound form can be washed and contamination that may adhere to it can be removed.

The core of the invention is the manner in which the biological material is released from the matrix. Owing to the fact that the matrix is compressible and porous, a solution of the isolated biological material can be obtained by compressing the matrix under conditions where the biological material is released from the matrix surface into an elution liquid. Compression means compressing the spatially extended structure together and thus pressing the liquid out of the inner volume of said structure. This increases the percentage of non-soluble material in the total structure while the percentage of the remaining inner volume is reduced. As proposed by the invention, the matrix is reduced by more than 40% and particularly preferred by more than 60%. The extent of the compression depends among other things also upon the desired amount of liquid which contains the biological material. The liquid emerging from the matrix can be obtained in any desired manner and be further processed.

An elution liquid as understood in the invention is a liquid where the biological material to be isolated can be dissolved. It has such a chemical composition that the balance between non-soluble material and solution is shifted to the side of the solution. If nucleic acids are then to be isolated, the solution used as elution solution is one with a lower salt concentration than the solution used to bind the nucleic acids to the non-soluble material.

The method of the invention is preferably carried out in a system. To accomplish this, the compressible porous matrix, together with the biological material bound thereto, is introduced into an elution vessel. The compressible porous matrix is preferably part of a vessel whose inner form matches the interior of the elution vessel. In order to release the biological material, elution liquid is added to the matrix and subsequently compressed with the aid of a piston; the possible outlet for the liquid is provided either in the piston or in the vessel containing the matrix or in the elution vessel or between these components.

The materials used to design the aforementioned vessels are preferably those that can be manufactured in an injection-molding procedure, e.g. plastics such as polystyrene, particularly preferred polypropylene, and optionally with suitable additives.

Figure 1:
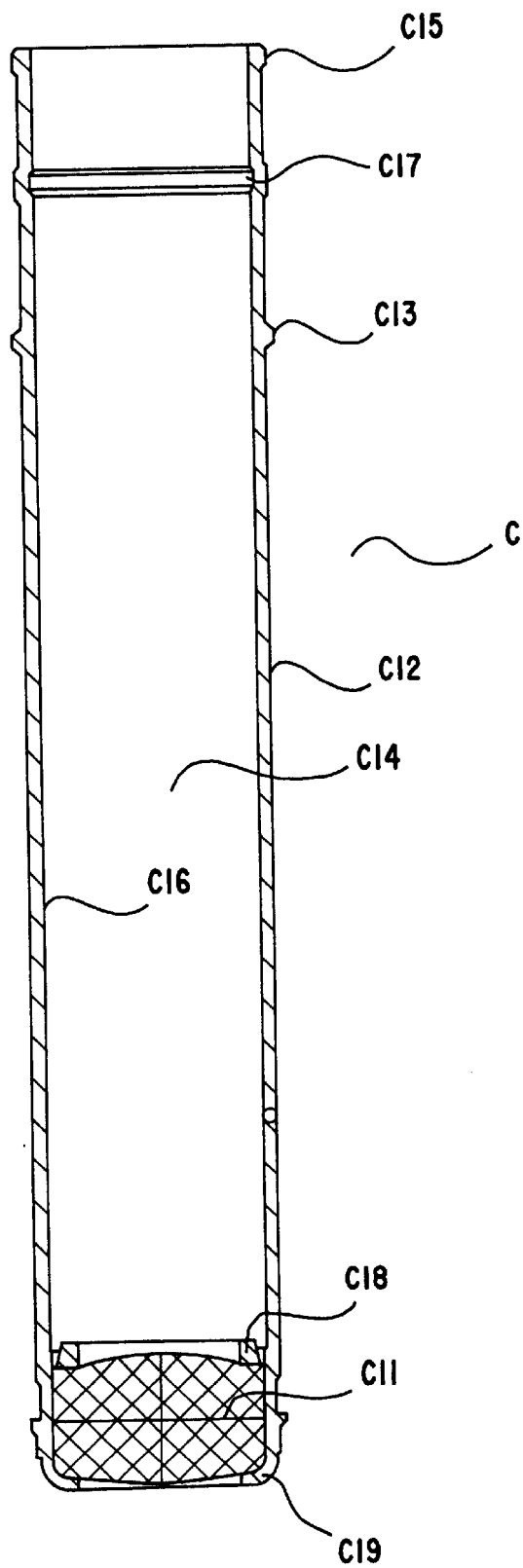
FIG. 1 is a structural form C configured as a vessel containing a compressible porous matrix in its lower portion (longitudinal section).

The following description further illustrates the objects listed in the figures in greater detail:

FIG. 1 is a longitudinal section of a structural form (C) which essentially has the form of a hollow cylinder with an upper and a lower opening. In the lower portion, the compressible porous matrix (C11) is fixed in position by tapering the cross section of the tube. Towards the bottom, the matrix is held by an edge (C19) and toward the top by means of a circumferential break-away bar (C18). By providing a desired breaking point along the inner wall (C16) of the structural form, this bar can be broken off and shifted in direction toward matrix (C11). The structural form (C) also has an inner contour (C12) and an interior which is configured as a hollow body (C14). Moreover, this structural form is provided with means (C17) to fix a piston (E) in the structural form. This means is preferably configured such that a piston is fixed in the position in which it compresses the matrix (C11). Moreover, the structural form (C) is preferably equipped with means (C15) to fix a lid on the upper opening. Further, it is also possible to provide means (C13) to fix the structural form in the elution vessel (D).

Figure 2:
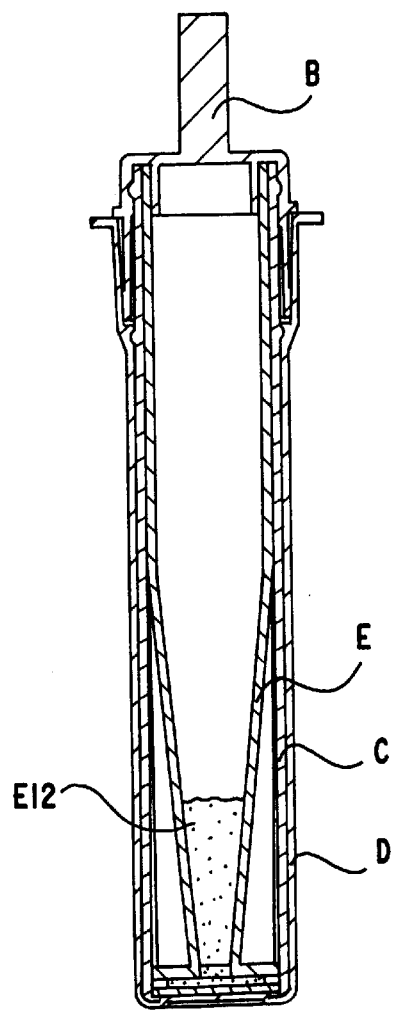
FIG. 2 is a system of the invention where the matrix is compressed (longitudinal section).

FIG. 2 is a particularly preferred system in accordance with the invention. It comprises the following components: elution vessel (D), structural form (C), piston (E), and lid (B). Lid (B) is configured such that it covers all the vessels. FIG. 2 shows the system in a form where the elution liquid that is originally contained in the matrix is pressed out of said matrix into the interior C12 of the piston.

Figure 3:
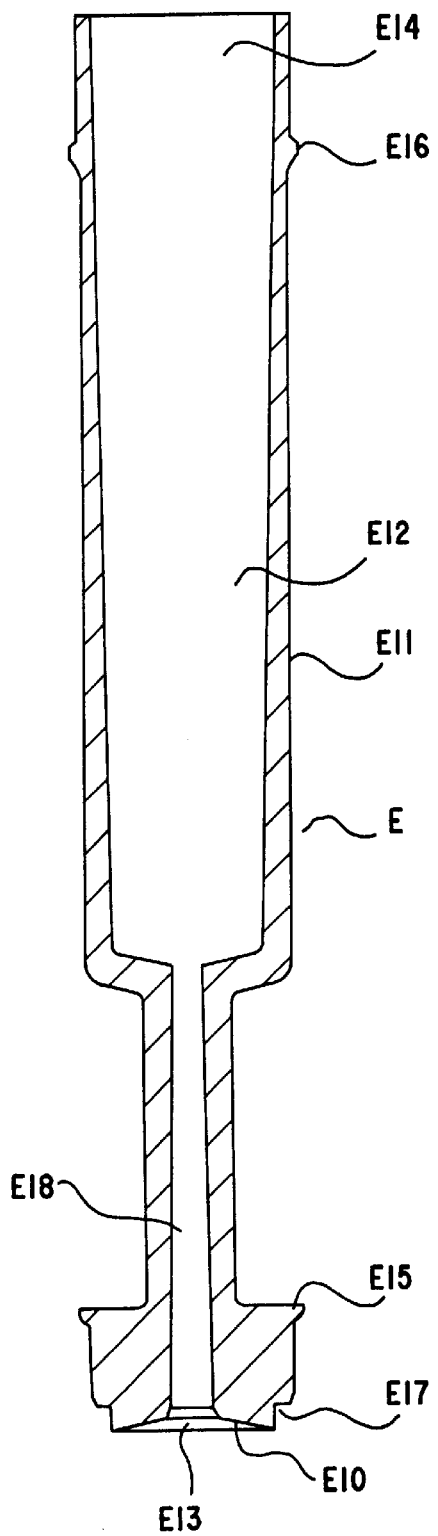
FIG. 3 is a piston in accordance with the invention to compress the matrix and receive elution liquid (longitudinal section).

FIG. 3 is a particularly preferred piston (E) to compress the porous matrix. It is characterized by a sealing ring (E15) in the lower portion which seals the space between the structural form (C) and elution vessel (D) thus preventing that any solution enters the so-generated capillary gap. In its upper area, piston (E) also has a snap-in ring (E16) which irreversibly fixes the piston in the structural form when the piston is introduced into the snap-in notch (C17) of the structural form (C). The so fixed piston (D) exerts sufficient pressure on the matrix to press liquid out of said matrix.

The pressure exerted onto the matrix can be adjusted in a certain range via the length of the snap-in connection of piston E and the position of the snap-in notch in the structural form (C). The lower geometry of piston (E) shows a pressing piston whose form-fitting geometry of the contact surface (E10) is suitable to ensure proper compression of the matrix. The form of the piston is configured such that the dead volume is minimized. Recesses (E17) act as a receptacle for broken off bars (C18).

In order to obtain and collect the solution pressed out of the matrix, the lower portion of the piston is provided with a transversal cylindrical bore; said bore has a relatively small diameter and a height that is suitable to receive the nucleic acid-containing solution that was pressed out, but also to remove liquid by means of a pipette. FIG. 3 shows a configuration where bore (E 18) is relatively narrow with respect to the possible internal volume of the piston. The one side of bore (E18) ends into opening (E13) in the contact surface and the other side into the interior of piston (E12).

The upper area of the piston is also a transversal bore which serves as a receptacle for the solution of biological material obtained; as compared to the lower part, it has a relatively large diameter and a suitable height. Diameter and height are selected such that they are suitable for introduction of the pipette into the interior (E12) and to remove liquid that has entered the interior via bore (E18).

Figure 4:
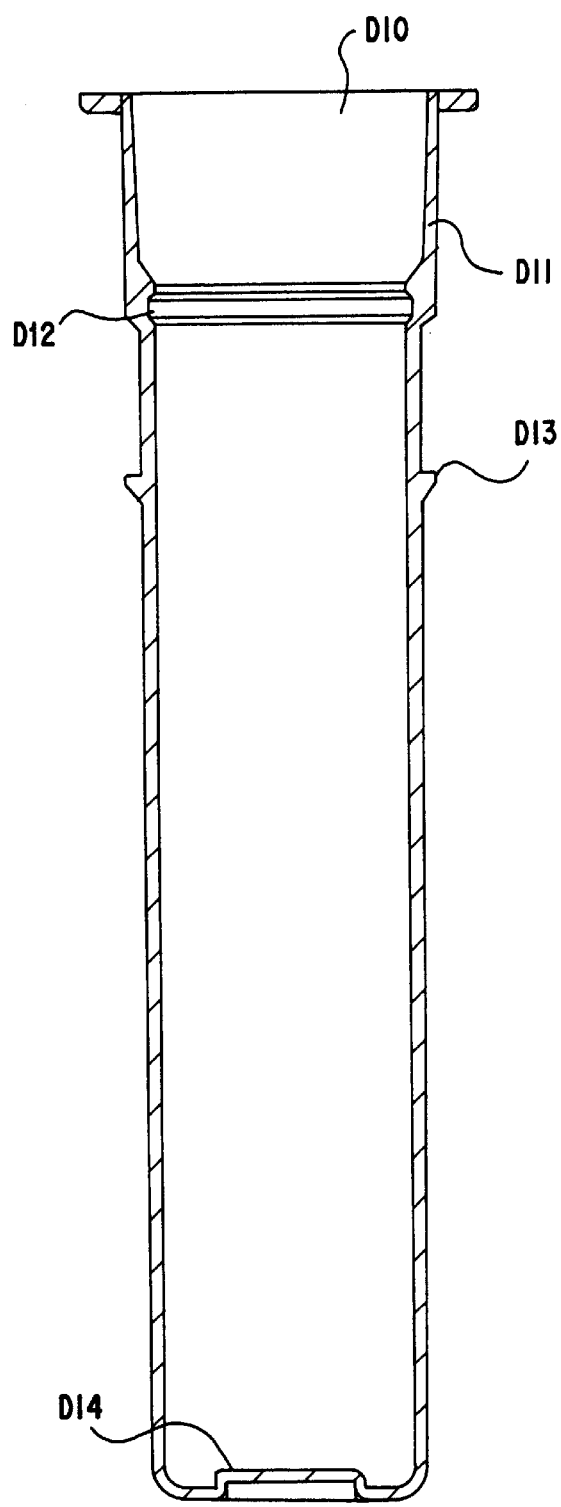
FIG. 4 shows an elution vessel D which is advantageously suitable for pressing a compressible porous matrix (longitudinal section).

FIG. 4 is a longitudinal section of a preferred elution vessel (D). It has an inlet opening (D10) for the introduction of liquids and/or other functional units into the elution vessel. Moreover, it has an inner edge (D11) to attach a lid (B). A snap-in notch (D12) is also provided in the upper part of the elution vessel; said notch serves to position the structural form via means (C13). Another preferred feature are means for attaching the elution vessel (D13) in an apertured plate of a suitable diameter. A particularly preferred feature is also the contact surface (D14) in the lower part of the elution vessel. By matching this surface to the lower part of the structural form, it is possible to reduce the dead volume inside the vessel. This leads to a particularly effective recovery of biological material.

Figure 5:
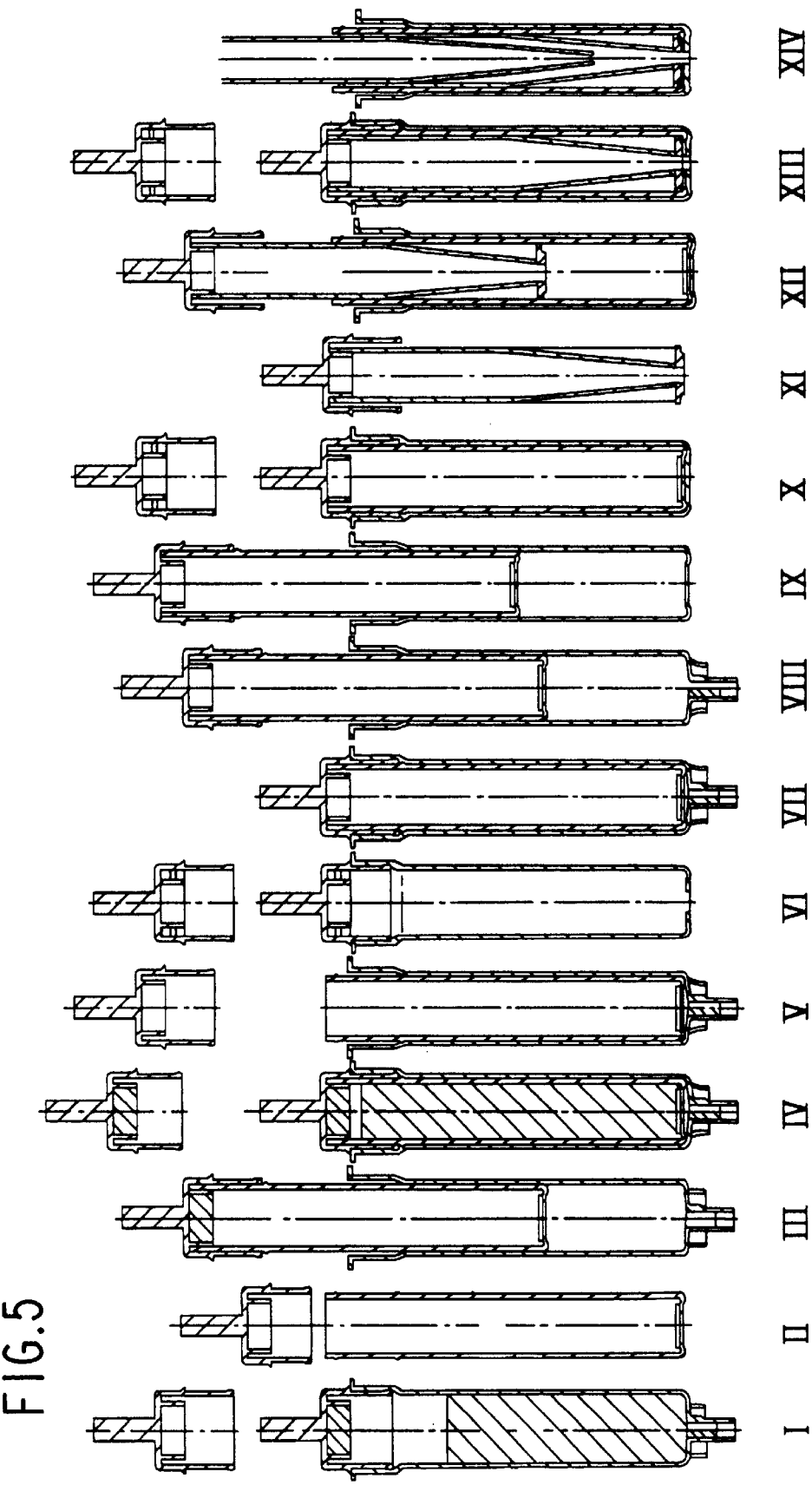
FIG. 5 is a diagrammatic representation of the operating steps and the structures involved in the method for isolating a biological material in accordance with the invention.

In a particular embodiment of the method of the invention for processing nucleic acid-containing sample solution, the following operating steps are carried out (see FIG. 5). In a first step (I) a cell-containing sample liquid is incubated in a sample vessel (A) with a material to which the cells are bound in order to obtain the nucleic acids. To accomplish this, said material can either exhibit specific binding properties for the surface of the cells, e.g. by immobilizing antibodies to surface antigens or an absorber material (A16, not shown); it is, however, also possible to provide a material with filter properties (A15, not shown) which retains the cells when liquid passes through the material, e.g. when removed from the sample vessel. Conditions for immobilizing cells on surfaces are known to the expert, e.g. from Methods in Enzymology, vol. 171, Biomembranes/Part R Transport Theory: Cell and Model Membranes, edited by Sidney Fleischer, Becca Fleischer, Department of Molecular Biology, Vanderbilt University, Nashville, Tenn.

During incubation, a lid (B) preferably closes the sample vessel to ensure active and passive protection from contamination.

In another step, the liquid is removed from the sample vessel while cells whose nucleic acids are to be isolated remain in the vessel where they are bound to the material. If the cell-binding material is a particle-type material, the cells can be retained in that the material is magnetic and a magnetic field is applied to the sample vessel from the outside; said field has to be strong enough to retain the particle-type material in the sample vessel when the liquid is removed. The liquid can be removed in different ways. It is, for example, possible to remove the liquid through an outlet opening (A11) which is spatially separated from the inlet opening (A10). If said outlet opening is located in a lower part of the sample vessel and below the retained cells, the liquid can be drawn off, e.g. by applying a minor vacuum. To accomplish this, a valve may be provided at the outlet opening to generate such a low pressure.

In order to remove other potentially interfering sample components from the cells, it is possible to provide one or several washing steps. To achieve this, washing liquid is filled into the sample vessel; said washing liquid dissolves possible contamination which, however, does not essentially affect the binding of the cells to the surface of the cell-binding material. Such washing solutions are known to the expert, e.g. from cell-separation protocols or corresponding cleaning kit protocols for nucleic acids. They basically depend on how the cells bind to the material.

After the last washing solution has been removed from the sample vessel (A), the purified, enriched cells are brought into contact with a suitable lysis liquid to release the nucleic acids from the cells. The reagents of this lysis solution largely depend on the type of immobilized cells. If the cells are bacteria, the lysis solution preferably contains proteinase K to digest the cell walls. Optionally, the lysis can be supported by heating or cooling and agitating the reaction mixture. If magnetic particles are used as cell-binding material, the mixing can also be accomplished with the aid of a magnet. Moreover, it is possible to mix the solution by shaking the sample vessel. Once digestion is completed, the nucleic acids to be isolated are freely accessible in the solution.

Even during lysis, it is preferred that the reaction vessel be closed by a lid in order to avoid contamination from the environment. After completion of the lysis, the lid is removed, preferably with the aid of a corresponding mechanical device. Subsequently, a structural form (C), whose outer contour (C12) matches the inner contour (A17) of the sample vessel, is introduced into the sample vessel which contains a mixture of digestion products of the cells and the nucleic acids. This structural form is hollow and sealed toward the sample vessel and toward the reaction mixture by means of a filter. The introduction of the structural form (C) is preferably accomplished with the aid of a component (B11) of lid (B) which also contains a component (B10) suitable to close the sample vessel. In this case, the structural form is taken up with the aid of a lid (II) and introduced in the sample vessel while the latter is closed. During this procedure, the reaction mixture can enter the hollow space (C14) of the structural form across filter (C11) (IV). By providing a filter, it is possible to prevent large particles from entering into the hollow space; if the filter already has nucleic acid binding properties, the nucleic acid can already be bound to the filter while the reaction mixture is passing through. In this case, it is expedient to select a glass fiber containing filter material.

In the next step, the remaining lysis reaction mixture is removed from the device consisting of A and C, e.g. by drawing off solution from the sample vessel through an outlet opening (A11) located in the lower portion of the vessel. The solution that has entered the hollow body (C14) of the structural form is, hence, also removed so that the filter more or less no longer contains any liquid. Subsequently, the so far used lid (B) is removed while the structural form (C) still remains in the sample vessel (where it is snapped into position) (V).

Simultaneously or subsequently, an elution vessel (D) is prepared to receive the structural form (C). A lid that can be provided on this vessel, if necessary, is removed (VI). Preferably, an elution solution is provided, e.g. by pipetting, in the elution vessel prior to transferring the structural form (C) into the elution vessel (D). The composition of the elution solution depends on how the nucleic acid is bound to the material in filter (C). It contains reagents which cause the immobilized nucleic acids to elute from the material, i.e. to be released therefrom. Lid (B) initially used to close the elution vessel, is now placed onto the sample vessel (A) with the structural form (C) (VII).

In order to take the structural form (C) out of sample vessel (A), the lid is first removed. The combination of lid and structural form is subsequently introduced into the elution vessel. In a preferred manner, the structural form (C) contains a means (C13K) to fix the structural form in position in the elution vessel (D). Owing to said means, the structural form (C) or the vessel (D) have to be destroyed in order to remove said structural form, or a force has to be applied which exceeds the force necessary to remove the lid (B) from structural form (C). The invention does not propose to remove the structural form from the elution vessel.

While the structural form (C) enters the elution vessel, already provided elution solution enters the matrix (C11) to release the immobilized nucleic acid from the solid matrix. Depending on the amount of prepared elution solution, either only the filter is impregnated with the elution solution or the elution solution enters the hollow body (C14) together with a released nucleic acid. For complete elution of the nucleic acids, the inner contour of the elution vessel should be configured to urge as tightly as possible against the outer contour of the structural form.

In a subsequent step, lid (B) is removed from the combination of structural form (C) and elution vessel (D) (X). Said lid (B) is used to take up a piston (E) (XI) and introduce said piston (E) into the hollow space of the structural form (C) (XII). Said lid engages piston (E) in the inside. The piston is pressed against the filter (C11) such that liquid which is present in the filter passes through an opening located in the contact surface into the interior of the piston. This procedure is particularly effective when the outer contour of the contact surface matches the inner contour of the structural form (C) in at least the area where said pressing is accomplished. Piston (E) can preferably be fixed in this position, e.g. by allowing it to snap into position. Since the so formed device is relatively well sealed by means of the lid, the nucleic acid containing solution can be stored in the device.

In order to remove the desired amount of nucleic acid solution, the lid can be removed (XIII) and the desired amount can be taken out via an opening in the interior of the piston, e.g. by means of pipetting (XIV). Subsequently, the lid can be placed back into position.

The method of the invention preferably comprises the following steps:

a) binding the biological material to a compressible matrix (C11)

b) adding an elution liquid into an elution vessel (D)

c) introducing the compressible porous matrix (C11), particularly preferred into a structural form (C)

d) introducing a piston (D) into the structural form (C) and the elution vessel (D); said piston has a contact surface suitable to compress the matrix; the piston has an interior (E12) to receive the liquid pressed out of the matrix e) allowing the piston to engage the structural form so that the matrix remains compressed.

The sequence of steps b and c may be exchanged in this procedure, if desired. The elution liquid containing with biological material which has entered the interior can subsequently be stored in the system (preferably with the lid being closed); or it can be removed with a pipette and processed in any desired way.

The method of the invention is particularly suitable for generating solutions of biological materials with relatively high concentrations. The invention allows the generation of nucleic acids from a matrix while the generation of aerosols is reduced. Moreover, the operating steps as proposed in the invention greatly facilitate automation of the process and method of isolating biological materials.

Another subject matter of the invention is a system for isolating a biological material which comprises the following components:

an elution vessel (D)

a compressible porous matrix, and a piston (E) to compress a matrix

Additional preferred features are described in the method of the invention.

The following examples describe the invention in greater detail.

EXAMPLE 1

A preferred embodiment of the piston is a hollow cylindrical plastic tube (E) having different diameters in its interior (D [bottom]=1 mm; D [top]=5 mm).

The piston can be characterized by the following dimensions:

| | |
|---|---|
| length: | 38.6 mm |
| outer diameter | 5.8 mm |
| inner diameter: | 5.0 mm |

The lower part of the piston is provided with a central bore (E 13); the top is receptacle (E 12) which is open toward the top.

At its top, the outer surface (E) has snap-in lips (E 16) to mount and position structural form (C). The circumferential snap-in lip is located 3,5 mm below the upper edge; it has a depth of 0.3 mm and a height of 0.25 mm. In its lower part, the piston is provided with sealing lips (E 15) which seal the piston with respect to the structural form. Said lips are elevated by 0.28 mm and have a width of 0.1 mm.

The upper opening of the piston has an inner geometry to link a functional lid (B) to an elution vessel (D). Piston (E) is configured such that it can be introduced into the structural form C to close together with lid B the entire system.

EXAMPLE 2
Biological materials/chemicals/devices

| | |
|---|---|
| Sample material: | Longitudinal standard II, Boehringer Mannheim |
| Binding buffer: | Qiagen AL 1/AL 2 (4 parts/1 part), manufactured by Qiagen |
| Washing buffer: | Qiagen AW buffer, manufactured by Qiagen |
| Elution buffer: | 10 mM Tris buffer, pH 9.0 |

Sample vessel (A)

Lid of sample vessel (B)

Structural form (C) having a porous matrix made of a glass fleece (C11)

Elution vessel (D)

Lid of elution vessel (E)

Pressing piston of structural form (F)

Preparing the sample solutions

| | | |
|---|---|---|
| Sample: | 200 μl | (6 μl longitudinal standard II dissolved in PBS buffer |
| Proteinase K | 25 μl | |
| Binding buffer | 200 μl | (AL 1 and AL 2 buffer mixed in a ratio of 4 + 1) |
| Ethanol | 210 μl | |
| Total volume | | |
| each batch: | 635 μl | |

How an example is carried out

Sample vessel (A) is filled with 200 μl of sample, 25 μl of proteinase K solution and 200 μl of binding buffer. Sample vessel (A) is closed with lid (B) of the sample vessel. The liquids are mixed in the closed vessel. Subsequently, the mixture is incubated at 70° C. for 10 min. (digestion of cells), followed by a cooling phase where it is cooled down to 20° C. in 3 minutes. Sample vessel (A) is opened, and 210 μl of ethanol are added. Sample vessel (A) is closed, and the solution is mixed.

Sample vessel (A) is opened. The lid (B) of the sample vessel is used to get the structural form (C) with a porous matrix out of its support. The structural form with the glass fleece matrix is introduced into the sample vessel which is filled with liquid through the inlet opening. While being introduced, the liquid present in the sample vessel (A) passes through the glass fleece from the bottom. The freely moving nucleic acid now binds to the glass fleece matrix. In the next step, the liquid present in the structural form (C) is drawn off towards the bottom. The liquid again passes through the glass fleece and nucleic acid which is not yet bound is now immobilized on the matrix.

The glass fleece matrix is washed twice with 500 μl of washing buffer. The buffer solution above the matrix is drawn off through the glass fleece. Subsequently, the matrix is dried with a purified nucleic acid at 50° C. for 3 minutes. Lid (B) of the sample vessel is discarded.

Using lid (E) of the elution vessel, the structural form (C) containing the nucleic acid is transferred from the sample vessel (D) into a prepared elution buffer with 200 μl elution buffer in it. The elution buffer releases the nucleic acid from the glass fleece matrix. The nucleic acid is partially located above the matrix.

By introducing a pressing piston (F) with the aid of the lid (E) of the elution vessel, the matrix in the structural form is compressed in order to minimize the dead volume of the nucleic acid solution.

Nucleic acid yields

The tests were carried out with two different nucleic acid sample concentrations. The following results could be determined:

| Test number | Isolated bound nucleic acid (μg) | Yield (%) |
|---|---|---|
| Test series 1: | | |
| Sample concentration: 6 μg of nucleic acid/200 μl elution solution | | |
| Test 1 | 1.4 μg | 22.9 |
| Test 2 | 1.6 μg | 27.5 |
| Test 3 | 1.2 μg | 23.8 |
| Test 4 | 1.5 μg | 29.8 |
| Test 5 | 1.6 μg | 35.2 |
| Test series 2: | | |
| Sample concentration: 20 μg of nucleic acid/200 μl elution solution | | |
| Test 1 | 3.7 μg | 28.0 |
| Test 2 | 6.4 μg | 38.8 |
| Test 3 | 4.8 μg | 40.0 |
| Test 4 | 4.1 μg | 30.3 |
| Test 5 | 5.1 μg | 37.8 |

| | List of reference numerals |
|---|---|
| A | Sample vessel |
| 10 | inlet opening |
| 11 | outlet opening |
| 12 | elastic material |
| 13 | lateral wall of outlet A 14 |
| 14 | outlet |
| 15 | filter material |
| 16 | absorber material |
| 17 | inner form |
| 18 | elastic tube |
| 19 | outer form |
| 20 | circumferential bar |
| 21 | holding element |
| 22 | element for positioning additional functional elements |
| 23 | spiral spring |
| 24 | sphere |
| 25 | needle |
| 26 | leaf spring |

-continued

List of reference numerals

| | |
|---|---|
| B | lid |
| 10 | component for closing sample vessel A |
| 11 | component for taking up structural form C |
| 12 | component for taking up the lid |
| 13 | aperture for air passage |
| 14 | filter element |
| 15 | element allowing B10 to engage in A |
| 16 | sealing lip |
| 17 | part of lid which covers opening |
| C | Structural form |
| 11 | porous matrix |
| 12 | outer contour |
| 13 | means for fixing the structural form in the elution vessel |
| 14 | hollow body |
| 15 | means for positioning lids |
| 16 | inner contour |
| 17 | means for positioning piston E, circumferentiai |
| 18 | circumferential break-away bar |
| 19 | edge |
| D | Elution vessel |
| 10 | inlet opening |
| 11 | edge for attaching lid |
| 12 | snap-in notch |
| 13 | means for positioning in an apertured plate |
| E | Piston |
| 10 | contact surface |
| 11 | outer contour |
| 12 | interior |
| 13 | opening in contact surface |
| 14 | opening for removal |
| 15 | seal |
| 16 | snap-in ring |
| 17 | recess |

We claim:

1. A method for isolating a biological material, comprising:

providing a hollow structural form having a first opening and a second opening and comprising an elution liquid-insoluble solid compressible porous matrix;

binding a biological material to the compressible porous matrix;

thereafter introducing the hollow structural form into an elution liquid-containing elution vessel through an opening therein, wherein the outer wall surface of the hollow structural form urges against the inner wall surface of the elution vessel, and wherein the first opening and the compressible porous matrix are configured to allow the passing of the elution liquid from the exterior of the hollow structural form through the first opening and into the compressible porous matrix;

thereafter inserting a piston, having a contact surface, into the hollow structural form through the second opening therein, and compressing the compressible porous matrix using the contact surface to force any elution liquid and biological material bound by the compressible porous matrix above the contact surface of the piston; and locking the contact surface in place using locking means, provided on the piston, for maintaining the compression of the compressible porous matrix by the contact surface.

2. The method of claim 1, wherein the biological material is a nucleic acid.

3. The method of claim 1, wherein the compressible porous matrix comprises glass fleece.

4. The method of claim 1, wherein the piston defines a hollow interior and has a first opening adjacent the contact surface, wherein the hollow interior receives the elution liquid and biological material forced from the compressible porous matrix through the inlet opening.

5. The method of claim 4, wherein the piston has a second opening configured to allow the removal of the biological material from the hollow interior, and the method further comprises, after the locking step, removing the biological material through the second opening without unlocking the locking means.

* * * * *